United States Patent

Panzeri et al.

Patent Number: 5,407,939
Date of Patent: Apr. 18, 1995

[54] FLUORINATED 17 β-SUBSTITUTED 4-AZA-5 α-ANDROSTAN-3-ONE DERIVATIVES

[75] Inventors: Achille Panzeri, Merate; Marcella Nesi; Enrico Di Salle, both of Milan, all of Italy

[73] Assignee: Farmitalia Carlo Erba S.R.L., Milan, Italy

[21] Appl. No.: 98,729

[22] Filed: Jul. 29, 1993

[30] Foreign Application Priority Data

Jul. 31, 1992 [GB] United Kingdom ............... 9216284

[51] Int. Cl.⁶ .................................... A61k 31/47
[52] U.S. Cl. ........................... 514/284; 546/77
[58] Field of Search ....................... 514/284; 546/77

[56] References Cited

U.S. PATENT DOCUMENTS

| 5,155,107 | 10/1992 | Panzeri et al. | 546/77 |
| 5,302,621 | 4/1994 | Kohima | 514/284 |
| 5,304,562 | 4/1992 | Biollaz | 546/77 |

FOREIGN PATENT DOCUMENTS

| 0155096 | 9/1985 | European Pat. Off. |
| 0200859 | 11/1986 | European Pat. Off. |
| 0484094 | 5/1992 | European Pat. Off. |

OTHER PUBLICATIONS

Liang et al. J. Steroid Biochem vol. 19 No. 1 pp. 385–390 (1983).
Lamb et al. The Prostate vol. 21 pp. 15–34 (1992).
Stinson, Chem. and Eng. News, Jun. 29, 1992 pp. 7 and 8.

*Primary Examiner*—Donald G. Daus
*Attorney, Agent, or Firm*—Oblon, Spivak, McClelland, Maier, & Neustadt

[57] ABSTRACT

Compounds of formula (I)

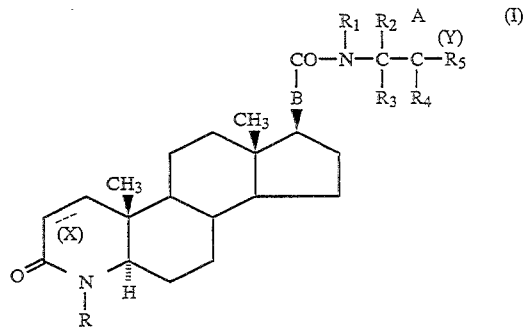

wherein:
the symbol ⸺ represents a single or a double bond;
B is a bond or a straight or branched $C_1$–$C_6$ alkylene chain;
R is hydrogen or $C_1$–$C_4$ alkyl;
$R_1$ is hydrogen, $C_1$–$C_6$ alkyl or benzyl;
$R_2$ is
  a) hydrogen, fluorine, $C_1$–$C_6$ alkyl, $C_5$–$C_7$ cycloalkyl or $C_6$–$C_9$ cycloalkylalkyl; or
  b) aryl or $C_7$–$C_{10}$ arylalkyl;
$R_3$ is
  a) hydrogen, fluorine or $C_1$–$C_4$ alkyl; or
  b) aryl or $C_7$–$C_{10}$ arylalkyl;
$R_4$ is hydrogen, fluorine, or is absent when Y is a double bond;
$R_5$ is hydrogen, fluorine or $C_1$–$C_6$ alkyl; and when Y is a single bond, A is hydrogen, fluorine or

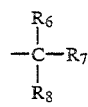

wherein each of $R_6$, $R_7$ and $R_8$ independently is hydrogen, fluorine or $C_1$–$C_6$ alkyl; and when Y is a double bond, A is a

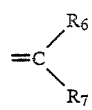

wherein each of $R_6$ and $R_7$ is independently hydrogen, fluorine or $C_1$–$C_6$ alkyl; with the proviso that at least one of the groups R, $R_1$, $R_2$, $R_3$, $R_4$, $R_5$ or A contains at least one fluorine atom.

6 Claims, No Drawings

FLUORINATED 17 β-SUBSTITUTED 4-AZA-5 α-ANDROSTAN-3-ONE DERIVATIVES

The present invention relates to fluorinated 17β-substituted 4-aza-5α-androstan-3-one derivatives, to a process for their preparation, and to pharmaceutical compositions containing them. These compounds act as inhibitors of androgen action, by means of testosterone 5α-reductase inhibition.

In certain androgen responsive tissues the action of testosterone is mediated primarily through its 5α-reduced metabolite, dihydrotestosterone (DHT) (Bruchowsky N., Wilson J. D.; J. Biol. Chem. 243, 5953, 1968). The conversion of testosterone to dihydrotestosterone is catalyzed by the enzyme 5α-reductase and if 5α-reductase is inhibited, the formation of dihydrotestosterone is reduced and its specific androgenic effect is attenuated or prevented.

The 5α-reductase inhibitors may find medical application for the treatment of hyperandrogenic conditions, e.g. certain prostatic diseases, such as benign prostatic hyperplasia and prostatic cancer, and certain skin-hair conditions, such as acne, seborrhoea, female hirsutism and male pattern baldness (Siiteri P. K., Wilson J. D., J. Clin. Invest. 49, 1737, 1970; Price V. H., Arch. Dermatol. III, 1496, 1975; Sandberg A. A., Urology 17, 34, 1981). Also breast cancer treatment can take advantage from use of 5α-reductase inhibitors as the said tumour is known to be aggravated by presence of androgens. Androst-4-en-3-one-17β-carboxylic acid and its methyl ester (Voigt and Hsia, Endocrinology, 92, 1216 (1973); Canadian Patent No. 970,692) are among the first steroidic compounds described as 5α-reductase inhibitors.

Two 5,10-secosteroids having a 3-keto-4,5-diene system in the expanded ring have been found to be selective inhibitors of rat epididymal 5α-reductase (Robaire et al., J. Steroid Biochem. 8, 307–310 (1977)).

The (20R)-4-diazo-21-hydroxy-20-methyl-5α-pregnan-3-one and its analogues are reported to be enzyme activated inhibitors of testosterone 5α-reductase (Blohm et al., Biochem. Biophys. Res. Comm. 95, 273–80 (1980); U.S. Pat. No. 4,317,817).

Another series of enzyme-directed irreversible inhibitors of 5α-reductase have been prepared by introducing a 6-methylene moiety into substrates type 3-keto-$\Delta^4$-progestins and androgens (Petrow et al., Steroids 38, 352–53 (1981); U.S. Pat. No. 4,396,615).

More recently unsaturated derivatives of 3-carboxy steroids have been reported as uncompetitive 5α-reductase inhibitors versus testosterone (Biorg. Chem. 17, 372–376 (1989); Eur. Pat. Appln. No. 0289327).

4-Aza steroids are by far the most studied steroid 5α-reductase inhibitors. The compounds known in the art are reported in a very large number of publications and patents. In particular the 17β-acylamides and their metabolites are described in: J. Med. Chem. 27, 1690–1701 (1984), J. Med. Chem. 29, 2298–2315 (1986), European Patent Application No. 0,004,949; U.S. Pat. No. 4,377,584; European Patent Application No. 0,155,096; U.S. Pat. No. 4,845,104; European Patent Application No. 0,462,662; European Patent Application No. 0,484,094 A2; U.S. Pat. No. 4,859,681; WO 12261.

The invention provides compounds of the following formula (I)

wherein:

the symbols ⁓ independently represent a single or a double bond;

B is a bond or a straight or branched $C_1$–$C_6$ alkylene chain;

R is a hydrogen atom or a $C_1$–$C_4$ alkyl group unsubstituted or substituted by one or more fluorine atoms;

$R_1$ is a hydrogen atom, a $C_1$–$C_6$ alkyl group unsubstituted or substituted by one or more fluorine atoms, or a benzyl group;

$R_2$ is a) a hydrogen atom, a fluorine atom, a $C_1$–$C_6$ alkyl group unsubstituted or substituted by one or more fluorine atoms, a $C_5$–$C_7$ cycloalkyl group or a $C_6$–$C_9$ cycloalkylalkyl group; or b) an aryl or $C_7$–$C_{10}$ arylalkyl group, either unsubstituted or ring substituted by one or more substituents chosen from halogen, $C_1$–$C_4$ alkyl, $C_1$–$C_4$ alkoxy, hydroxy and trifluoromethyl;

$R_3$ is a) a hydrogen atom, a fluorine atom or a $C_1$–$C_4$ alkyl group unsubstituted or substituted by one or more fluorine atoms; or b) an aryl or $C_7$–$C_{10}$ arylalkyl group, either unsubstituted or ring substituted by one or more substituents chosen from halogen, $C_1$–$C_4$ alkyl, $C_1$–$C_4$ alkoxy, hydroxy and trifluoromethyl;

$R_4$ is a hydrogen atom or a fluorine atom, or is absent when Y is a double bond;

$R_5$ is a hydrogen atom, a fluorine atom or a $C_1$–$C_6$ alkyl group unsubstituted or substituted by one or more fluorine atoms; and when Y is a single bond, A is hydrogen, fluorine or a $$-\underset{R_8}{\underset{|}{\overset{R_6}{\overset{|}{C}}}}-R_7$$

group wherein each of $R_6$, $R_7$ and $R_8$ independently is hydrogen, fluorine or a $C_1$–$C_6$ alkyl group unsubstituted or substituted by one or more fluorine atoms; or when Y is a double bond, A is a $$=C\diagup^{R_6}_{\diagdown R_7}$$

group wherein each of $R_6$ and $R_7$ is independently hydrogen, fluorine or a $C_1$–$C_6$ alkyl group unsubstituted or substituted by one or more fluorine atoms;

with the proviso that at least one of the groups R, $R_1$, $R_2$, $R_3$, $R_4$, $R_5$ and A contains at least one fluorine atom.

In the formulae of this specification the dotted line ("''''''") indicates a substituent in the α-configuration, i.e. below the plane of the ring, and the wedged line (▼) indicates a substituent in the β-configuration, i.e. above the plane of the ring. The configuration of the chiral centres in the side chain is unspecified; the invention includes both the single "R" or "S" epimers and their "RS" mixtures.

The metabolites and the metabolic precursors of the compounds of formula (I) are within the scope of the present invention.

In this specification the alkyl groups and the aliphatic portions of the cycloalkylalkyl groups may be a straight or branched chain.

A $C_1$–$C_4$ alkyl group may be, for example, methyl, ethyl, isopropyl, n-butyl or tert-butyl. The $C_1$–$C_4$ alkyl group may be unsubstituted or substituted by one or more, preferably one, two or three, fluorine atoms and may be, for example, trifluoromethyl, 2,2,2-trifluoroethyl, fluoromethyl or difluoromethyl.

A $C_1$–$C_6$ alkyl group may be, for example, methyl, ethyl, n-propyl, isopropyl, n-butyl, iso-butyl, sec-butyl, tert-butyl, n-pentyl, iso-pentyl, neo-pentyl, n-hexyl or iso-hexyl. The $C_1$–$C_6$ alkyl group may be unsubstituted or substituted by one or more, preferably, one to six or one, two or three, fluorine atoms and may be, for example, fluoromethyl, difluoromethyl, trifluoromethyl, 2,2,2-trifluoroethyl, 3,3,3-trifluoroprop-1-yl or 4,4,4-trifluorobut-1-yl, 1-trifluoromethyleth-1-yl, 2-trifluoromethylprop-1-yl, 1,1,1,3,3,3-hexafluoroprop-2-yl, 4,4,5,5,5-pentafluoropentyl or 3,3,3,2,2-pentafluoroprop-1yl.

A $C_5$–$C_7$ cycloalkyl group may be, for example, cyclopentyl, cyclohexyl or cycloheptyl, preferably cyclohexyl.

A $C_6$–$C_9$ cycloalkylalkyl group may be, for example, ($C_5$–$C_7$ cycloalkyl) alkyl, preferably ($C_5$–$C_7$ cycloalkyl) methyl or ($C_5$–$C_7$ cycloalkyl) ethyl, in particular, cyclohexylmethyl, cyclohexylethyl or cycloheptylmethyl, preferably cyclohexylmethyl.

An aryl group may be, for example, phenyl unsubstituted or substituted by one or more, preferably one, chloro, bromo, fluoro, $C_1$–$C_4$ alkyl, preferably methyl, $C_1$–$C_4$ alkoxy, preferably methoxy, hydroxy or trifluoromethyl groups, in particular, 4-methylphenyl, 4-hydroxyphenyl, 4-methoxyphenyl, 4-trifluoromethylphenyl or 4-fluorophenyl.

A $C_7$–$C_{10}$ arylalkyl group may be, for example, phenyl($C_1$–$C_4$ alkyl), preferably benzyl, unsubstituted or ring substituted by one or more, preferably one or two, chloro, bromo, fluoro, $C_1$–$C_4$ alkoxy preferably methoxy, hydroxy or trifluoromethyl groups, in particular 4-hydroxybenzyl, 4-methoxybenzyl, 4-hydroxy-3-methoxybenzyl, 3,4-dimethoxybenzyl, 4-trifluoromethylbenzyl, 2-fluorobenzyl, 3-fluorobenzyl, 4-fluorobenzyl or 3-fluoro-4-hydroxybenzyl.

A $C_1$–$C_6$ straight or branched alkylene chain may be, for example, a straight or branched $C_1$–$C_4$ alkylene chain, in particular, e.g.,

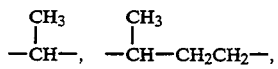

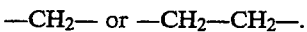

—$CH_2$— or —$CH_2$—$CH_2$—.

When R is a $C_1$–$C_4$ alkyl group unsubtituted or substituted by one or more fluorine atoms, it is preferably methyl or 2,2,2-trifluoroethyl;

when $R_1$ is a $C_1$–$C_6$ alkyl group unsubstituted or substituted by one or more fluorine atoms, it is preferably methyl, ethyl, isopropyl, isobutyl, sec-butyl, tert-butyl, 2,2,2-trifluoroeth-1-yl, 1-trifluoromethyleth-1-yl, 1,1,1,3,3,3-hexafldoroprop-2-yl, 2-trifluoromethylprop-1-yl or 2,2,3,3,3-pentafluoroprop-1-yl;

when $R_2$ is a $C_1$–$C_6$ alkyl group unsubstituted or substituted by one or more fluorine atoms, it is preferably methyl, isopropyl, isobutyl, sec-butyl, tert-butyl, fluoromethyl, trifluoromethyl, 2,2,2-trifluoroeth-1-yl, 1-trifluoromethyleth-1-yl, 3,3,3-trifluoropropyl, 1,1,1,3,3,3-hexafluoroprop-2-yl, 2-trifluoromethylprop-1-yl or 4,4,4-trifluorobutyl;

when $R_2$ is a $C_5$–$C_7$ cycloalkyl group it is preferably cyclohexyl;

when $R_2$ is a $C_6$–$C_9$ cycloalkylalkyl group, it is preferably cyclohexylmethyl;

when $R_2$ is an aryl group, it is preferably phenyl;

when $R_2$ is an unsubstituted $C_7$–$C_{10}$ arylalkyl group, it is preferably benzyl;

when $R_2$ is a substituted $C_7$–$C_{10}$ arylalkyl group, it is preferably p-trifluoromethylbenzyl;

when $R_3$ is a $C_1$–$C_4$ alkyl group unsubstituted or substituted by one or more fluorine atoms, it is preferably methyl, fluoromethyl or trifluoromethyl;

when $R_3$ is an aryl group, it is preferably phenyl;

when $R_3$ is an unsubstituted $C_7$–$C_{10}$ arylalkyl group it is preferably benzyl;

when $R_3$ is a substituted $C_7$–$C_{10}$ arylalkyl group, it is preferably p-trifluoromethylbenzyl;

when $R_5$ is a $C_1$–$C_6$ alkyl group unsubstituted or substituted by one or more fluorine atoms, it is preferably methyl, n-butyl, trifluoromethyl or pentafluoroethyl; when A is a

group, it is preferably methyl, fluoromethyl, difluoromethyl, trifluoromethyl, ethyl or n-propyl;

when A is a

group it is preferably

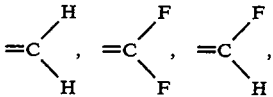

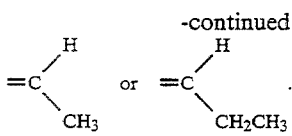

Preferred compounds of formula (I) are those wherein:
1) the symbol ⁻⁻⁻ represents a single or a double bond;
B is a bond;
R is hydrogen, methyl or 2,2,2-trifluoroethyl;
$R_1$ is hydrogen;
$R_2$ is hydrogen, methyl, isopropyl, isobutyl, sec-butyl, tert-butyl, trifluoromethyl, 3,3,3-trifluoropropyl, 4,4,4-trifluorobutyl, 2-trifluoromethylprop-1-yl, 1-trifluoromethyleth-1-yl, fluoromethyl, benzyl or phenyl;
$R_3$ is hydrogen or methyl;
$R_4$ is hydrogen;
$R_5$ is methyl, trifluoromethyl or n-butyl;
Y is a single bond; and
A is a group

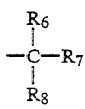

wherein $R_6$ is hydrogen or fluorine and $R_7$ and $R_8$ are both hydrogen or fluorine atoms; with the proviso that at least one of the groups R, $R_2$, $R_5$ or A contains at least one fluorine atom;
2) the symbol ⁻⁻⁻ represents a single or a double bond;
B is a bond;
R is hydrogen, methyl or 2,2,2-trifluoroethyl;
$R_1$ is hydrogen;
$R_2$ is hydrogen, methyl, isopropyl, isobutyl, sec-butyl, tert-butyl, trifluoromethyl, 3,3,3-trifluoropropyl, 4,4,4-trifluorobutyl, 2-trifluoromethylprop-1-yl, 1-trifluoromethyleth-1-yl, fluoromethyl, benzyl, phenyl;
$R_3$ is hydrogen;
$R_4$ is absent;
$R_5$ is methyl, trifluoromethyl or n-butyl;
Y is a double bond; and
A is a group

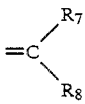

wherein $R_7$ and $R_8$ are both hydrogen atoms or fluorine atoms;
with the proviso that at least one of the groups R, $R_2$, $R_5$ or A contains at least one fluorine atom.
3) the symbol ⁻⁻⁻ represents a single or a double bond;
R is hydrogen, methyl or 2,2,2-trifluoroethyl;
$R_1$ is hydrogen, 2,2,2-trifluoroethyl, 2,2,3,3,3-pentafluoroprop-1-yl, methyl, ethyl, isopropyl, isobutyl or tert-butyl;
$R_2$ is hydrogen, methyl, isopropyl, fluoromethyl, trifluoromethyl, benzyl or phenyl;
$R_3$ is hydrogen, methyl, fluoromethyl, trifluoromethyl, benzyl or phenyl;
$R_4$ is hydrogen or fluorine;
$R_5$ is hydrogen, fluorine or trifluoromethyl;
B is a bond;
Y is a single bond; and
A is hydrogen or fluorine;
with the proviso that at least one of the groups R, $R_1$, $R_2$, $R_3$, $R_4$, $R_5$ or A contains at least one fluorine atom.

Examples of preferred compounds of the invention are:
1) N-(4,4,4-trifluoro-3-methyl-but-2-yl) 4-methyl-3-oxo-4-aza-5α-androstane-17β-carboxamide;
2) N-(1,1,1-trifluoro-3-methyl-but-2-yl) 4-methyl-3-oxo-4-aza-5α-androstane-17β-carboxamide;
3) N-(4,4,4-trifluoro-3-methyl-but-2-yl) 3-oxo-4-aza-5α-androstane-17β-carboxamide;
4) N-(1,1,1-trifluoro-3-methyl-but-2-yl) 3-oxo-4-aza-5α-androstane-17β-carboxamide;
5) N-(5-methyl-2-difluoromethyl-hex-3-yl) 4-methyl-3-oxo-4-aza-5α-androstane-17β-carboxamide;
6) N-(3-difluoromethyl-hept-2-yl) 4-methyl-3-oxo-4-aza-5α-androstane-17β-carboxamide;
7) N-(5-methyl-2-difluoromethyl-hex-3-yl) 3-oxo-4-aza-5α-androstane-17β-carboxamide;
8) N-(3-difluoromethyl-hept-2-yl) 3-oxo-4-aza-5α-androstane-17β-carboxamide;
9) N-(4,4,4-trifluoro-3-methylene-but-2-yl) 4-methyl-3-oxo-4-aza-5α-androstane-17β-carboxamide;
10) N-(1,1,1-trifluoro-3-methylene-but-2-yl) 4-methyl-3-oxo-4-aza-5α-androstane-17β-carboxamide;
11) N-(4,4,4-trifluoro-3-methylene-but-2-yl) 3-oxo-4-aza-5α-androstane-17β-carboxamide;
12) N-(1,1,1-trifluoro-3-methylene-but-2-yl) 3-oxo-4-aza-5α-androstane-17β-carboxamide;
13) N-(5-methyl-2-difluoromethylene-hex-3-yl) 4-methyl-3-oxo-4-aza-5α-androstane-17β-carboxamide;
14) N-(3-difluoromethylene-hept-2-yl) 4-methyl-3-oxo-4-aza-5α-androstane-17β-carboxamide;
15) N-(5-methyl-2-difluoromethylene-hex-3-yl) 3-oxo-4-aza-5α-androstane-17β-carboxamide;
16) N-(3-difluoromethylene-hept-2-yl) 3-oxo-4-aza-5α-androstane-17β-carboxamide;
17) N-(2,2,2-trifluoroethyl) 3-oxo-4-aza-5α-androst-1-end-17β-carboxamide;
18) N,N-di-(2,2,2-trifluoroethyl) 3-oxo-4-aza-5α-androst-1-ene-17β-carboxamide;
19) N-(1,1,1,3,3,3-hexafluoroprop-2-yl) 3-oxo-4-aza-5α-androst-1-ene-17β-carboxamide;
20) N,N-di-(1,1,1,3,3,3-hexafluoroprop-2-yl) 3-oxo-4-aza-5α-androst-1-ene-17β-carboxamide;
21) N-methyl-N-(2,2,2-trifluoroethyl) 3-oxo-4-aza-5α-androst-1-ene-17β-carboxamide;
22) N-isobutyl-N-(2,2,2-trifluoroethyl) 3-oxo-4-aza-5α-androst-1-ene-17β-carboxamide;
23) N-(1-fluoro-2-methyl-prop-2-yl) 3-oxo-4-aza-5α-androst-1-ene-17β-carboxamide;
24) N-(1,3-difluoro-2-methyl-prop-2-yl) 3-oxo-4-aza-5α-androst-1-ene-17β-carboxamide;
25) N-(1,3-difluoro-2-fluoromethyl-prop-2-yl) 3-oxo-4-aza-5α-androst-1-ene-17β-carboxamide;
26) N-(5,5,5-trifluoro-2,4-dimethylpent-3-yl) 3-oxo-4-aza-5α-androstane-17β-carboxamide;
27) N-(4,4,4-trifluoro-2,3-dimethylbut-2-yl) 3-oxo-4-aza-5α-androstane-17β-carboxamide;
28) N-(4,4,4-trifluoro-3-methylbut-2-yl) 3-oxo-4-aza-5α-androst-1-ene-17β-carboxamide;
29) N-(5,5,5-trifluoro-2,4-dimethylpent-3-yl) 3-oxo-4-aza-5α-androst-1-ene-17β-carboxamide;
30) N-(4,4,4-trifluoro-2,3-dimethylbut-2-yl) 3-oxo-4-aza-5α-androst-1-ene-17β-carboxamide;

31) N-(4,4,4-trifluorobut-2-yl) 3-oxo-4-aza-5α-androst-1-ene-17β-carboxamide;

32) N-(5,5,5-trifluoro-2-methylpent-3-yl) 3-oxo-4-aza-5α-androst-1-ene-17β-carboxamide;

33) N-(4,4,4-trifluoro-2-methylbut-2-yl) 3-oxo-4-aza-5α-androst-1-ene-17β-carboxamide;

34) N-(4,4,4-trifluoro-3-methylene-but-2-yl) 3-oxo-4-aza-5α-androst-1-ene-17β-carboxamide;

35) N-(5,5,5-trifluoro-4-methylene-2-methylpent-3-yl) 3-oxo-4-aza-5α-androst-1-ene-17β-carboxamide;

42) N-(2,2,2-trifluoro-1,1-diphenylethyl) 3-oxo-4-aza-5α-androst-1-ene-17β-carboxamide;

43) N-(1,1,1-trifluoro-2-methylprop-2-yl) 3-oxo-4-aza-5α-androst-1-ene-17β-carboxamide; and 44) N-(1,1,1,3,3,3-hexafluoro-2-methylpropyl) 3-oxo-4-aza-5α-androst-1-ene-17β-carboxamide.

The structural formulae of the above listed compounds, according to their numbers, are tabulated below with reference to the substituents as defined in formula (I):

| | (Y) | A | $R_5$ | B | (X) | R | $R_1$ | $R_2$ | $R_3$ | $R_4$ |
|---|---|---|---|---|---|---|---|---|---|---|
| 1 | single | $CH_3$ | $CF_3$ | bond | single | $CH_3$ | H | $CH_3$ | H | H |
| 2 | single | $CH_3$ | $CH_3$ | bond | single | $CH_3$ | H | $CF_3$ | H | H |
| 3 | single | $CH_3$ | $CF_3$ | bond | single | H | H | $CH_3$ | H | H |
| 4 | single | $CH_3$ | $CH_3$ | bond | single | H | H | $CF_3$ | H | H |
| 5 | single | $CHF_2$ | $CH_3$ | bond | single | $CH_3$ | H | i-but | H | H |
| 6 | single | $CHF_2$ | n-but | bond | single | $CH_3$ | H | $CH_3$ | H | H |
| 7 | single | $CHF_2$ | $CH_3$ | bond | single | H | H | i-but | H | H |
| 8 | single | $CHF_2$ | n-but | bond | single | H | H | $CH_3$ | H | H |
| 9 | double | $CH_2$ | $CF_3$ | bond | single | $CH_3$ | H | $CH_3$ | H | — |
| 10 | double | $CH_2$ | $CH_3$ | bond | single | $CH_3$ | H | $CF_3$ | H | — |
| 11 | double | $CH_2$ | $CF_3$ | bond | single | H | H | $CH_3$ | H | — |
| 12 | double | $CH_2$ | $CH_3$ | bond | single | H | H | $CF_3$ | H | — |
| 13 | double | $CF_2$ | $CH_3$ | bond | single | $CH_3$ | H | i-but | H | — |
| 14 | double | $CF_2$ | n-but | bond | single | $CH_3$ | H | $CH_3$ | H | — |
| 15 | double | $CF_2$ | $CH_3$ | bond | single | H | H | i-but | H | — |
| 16 | double | $CF_2$ | n-but | bond | single | H | H | $CH_3$ | H | — |
| 17 | single | F | F | bond | double | H | H | H | H | F |
| 18 | single | F | F | bond | double | H | $CF_3$—$CH_2$ | H | H | F |
| 19 | single | F | F | bond | double | H | H | $CF_3$ | H | F |
| 20 | single | F | F | bond | double | H | $CF_3$\\CH—/$CF_3$ | $CF_3$ | H | F |
| 21 | single | F | F | bond | double | H | $CH_3$ | H | H | F |
| 22 | single | F | F | bond | double | H | i-Bu | H | H | F |
| 23 | single | H | F | bond | double | H | H | $CH_3$ | $CH_3$ | H |
| 24 | single | H | F | bond | double | H | H | $CH_2F$ | $CH_3$ | H |
| 25 | single | H | F | bond | double | H | H | $CH_2F$ | $CH_2F$ | H |
| 26 | single | $CH_3$ | $CF_3$ | bond | single | H | H | i-Pr | H | H |
| 27 | single | $CH_3$ | $CF_3$ | bond | single | H | H | $CH_3$ | $CH_3$ | H |
| 28 | single | $CH_3$ | $CF_3$ | bond | double | H | H | $CH_3$ | H | H |
| 29 | single | $CH_3$ | $CF_3$ | bond | double | H | H | i-Pr | H | H |
| 30 | single | $CH_3$ | $CF_3$ | bond | double | H | H | $CH_3$ | $CH_3$ | H |
| 31 | single | H | $CF_3$ | bond | double | H | H | $CH_3$ | H | H |
| 32 | single | H | $CF_3$ | bond | double | H | H | i-Pr | H | H |
| 33 | single | H | $CF_3$ | bond | double | H | H | $CH_3$ | $CH_3$ | H |
| 34 | double | $CH_2$ | $CF_3$ | bond | double | H | H | $CH_3$ | H | — |
| 35 | double | $CH_2$ | $CF_3$ | bond | double | H | H | i-Pr | H | — |
| 36 | double | $CH_2$ | $CF_3$ | bond | double | H | H | $CH_3$ | $CH_3$ | — |
| 37 | single | F | F | bond | single | $CH_3$ | H | H | H | F |
| 38 | single | F | F | bond | double | H | i-Pr | H | H | F |
| 39 | single | F | $CF_3$ | bond | double | H | i-Pr | H | H | F |
| 40 | single | F | F | bond | double | H | H | Ph | H | F |
| 41 | single | F | F | bond | double | H | H | Ph | $CH_3$ | F |
| 42 | single | F | F | bond | double | H | H | Ph | Ph | F |
| 43 | single | F | F | bond | double | H | H | $CH_3$ | $CH_3$ | F |
| 44 | single | F | F | bond | double | H | H | $CH_3$ | $CF_3$ | F |

36) N-(4,4,4-trifluoro-3-methylene-2-methylbut-2-yl) 3-oxo-4-aza-5α-androst-1-ene-17β-carboxamide;

37) N-(2,2,2-trifluoroethyl) 4-methyl-3-oxo-4-aza-5α-androstane-17β-carboxamide;

38) N-isopropyl-N-(2,2,2-trifluoroethyl) 3-oxo-4-aza-5α-androst-1-ene-17β-carboxamide;

39) N-isopropyl-N-(2,2,3,3,3-pentafluoropropyl) 3-oxo-4-aza-5α-androst-1-ene-17β-carboxamide;

40) N-(2,2,2-trifluorophenylethyl) 3-oxo-4-aza-5α-androst-1-ene-17β-carboxamide;

41) N-(1,1,1-trifluoro-2-phenylprop-2-yl) 3-oxo-4-aza-5α-androst-1-ene-17β-carboxamide;

The compounds of formula (I) may be obtained by a process comprising:

A) reacting a compound of formula (II)

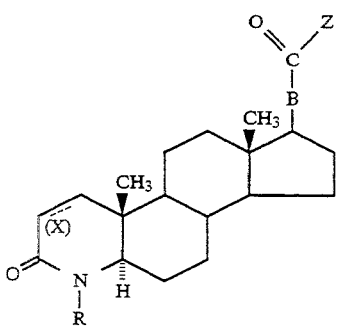 (II)

wherein the symbol ⁓, R and B are as defined above and Z is an activating group of the carboxy function with a compound of formula (III) or a salt thereof

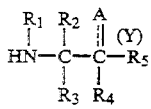 (III)

wherein the symbol ⁓, R₁, R₂, R₃, R₄, R₅ and A are as defined above, so obtaining a compound of formula (I) wherein the symbol ⁓, R, R₁, R₂, R₃, R₄, R₅, B and A are as defined above; or B) reacting a compound of formula (IV)

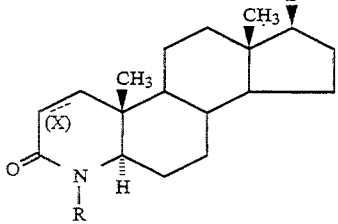 (IV)

wherein the symbol ⁓, R, R₁, R₂, R₃ and B are as defined above and R₅ is a $C_1$–$C_6$ alkyl group unsubstituted or substituted by one or more fluorine atoms with a compound of formula (V) or (VI)

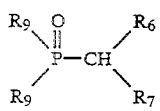 (V)

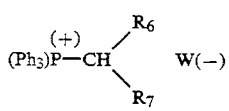 (VI)

wherein R₆ and R₇ are as defined above, each R₉ is independently methoxy, ethoxy or phenyl, and W is a halogen atom, so obtaining a compound of formula (I) wherein the symbol ⁓, R, R₁, R₂, R₃ and B are as defined above, R₅ is a $C_1$–$C_6$ alkyl group unsubstituted or substituted by one or more fluorine atoms, Y is a double bond, R₄ is absent and A is a

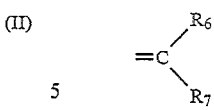

group wherein R₆ and R₇ are as defined above; or
C) reducing a compound of formula (VII)

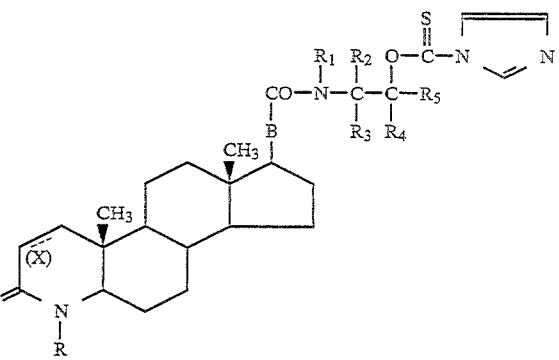 (VII)

wherein the symbol ⁓, R, R₁, R₂, R₃, R₅ and B are as defined above and R₄ is hydrogen, so obtaining a compound of formula (I) wherein the symbol ⁓, R, R₁, R₂, R₃, R₅ and B are as defined above, R₄ and A are both hydrogen and Y is a single bond; and, if desired, D) hydrogenating a compound of formula (I) wherein ⁓, R, R₁, R₂, R₃ and B are as defined above, R₄ is absent, R₅ is hydrogen or $C_1$–$C_6$ alkyl group unsubstituted or substituted by one or more fluorine atoms, Y is a double bond and A is a group

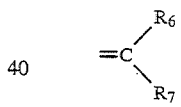

wherein R₆ and R₇ are as defined above so obtaining a compound of formula (I) wherein X and Y are single bonds, R, R₁, R₂, R₃ and B are as defined above, R₄ is hydrogen, R₅ is hydrogen or a $C_1$–$C_6$ alkyl group unsubstituted or substituted by one or more fluorine atoms, and A is a group

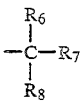

wherein R₈ is a hydrogen atom and R₆ and R₇ are as defined above; and/or

E) dehydrogenating a compound of formula (I) wherein the ⁓, R, R₁, R₂, R₃, R₄, R₅, B and A are as defined above, and X is a single bond so obtaining a compound of formula (I) wherein Y, R₁, R₂, R₃, R₄, R₅, B and A are as defined above and X is a double bond; and, if desired, separating a mixture of isomers of formula (I) into the single isomers.

In the compound of formula (II) the Z group is an activating group of the carboxy function useful in the formation of amidic and peptidic linkages; it may be for instance one of the following groups:

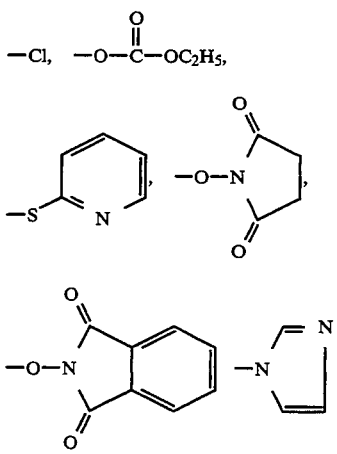

The reaction of a compound of formula (II) with a compound of formula (III), according to the process variant A), may be, e.g., carried out in a solvent such as, for example, methylene chloride, ethyl acetate, tetrahydrofuran, dimethylformamide, benzene or toluene at a temperature ranging from about 0° C. to about 100° C., for a time varying from about 1 hour to about 48 hours.

If the compound of formula (III) is in the salt-form a stoichiometric amount of an organic base, such as, for example, pyridine or a tri-$C_1$-$C_6$-alkylamine, preferably triethylamine, has to be added to the reaction mixture.

The reaction of a compound of formula (IV) with a compound of formula (V) according to the process variant B), may be carried out in the usual conditions of the Horner-Wadsworth-Emmons reaction.

For example, the reaction may be carried out by reacting the compound of formula (V) dissolved in an anhydrous solvent such as, for example, ethyl ether or tetrahydrofuran, with a lithium alkylamide such as, for example, lithium diisopropylamide or an alkyl lithium derivative, such as butyl lithium or sodium hydride, at a temperature from about −78° C. to about 0° C., under an inert atmosphere of nitrogen or argon, for a time varying from half an hour to 3 hours, then the compound of formula (IV) dissolved in tetrahydrofuran is added to the reaction mixture and the reaction continued at a temperature varying from room temperature to the reflux temperature of the reaction mixture, for a time varying from some hours to 1 or 2 days.

In the compounds of formula (VI), W is a halogen atom, preferably iodine. The reaction of a compound of formula (IV) with a compound of formula (VI), according to the process variant B), may be carried out in the usual conditions of the Wittig reaction.

For example, the reaction may be carried out reacting the compound of formula (VI) with a strong base such as, for example, a lithium alkyl amide (e.g. lithium diisopropylamide), or an alkyl lithium (e.g. butyl lithium) or an alkaline metal hydride (e.g. sodium hydride) or an alkaline metal alkoxide (e.g. potassium tert-butoxide) in a solvent such as, for example, diglyme, dimethylsulfoxide (DMSO), tetrahydrofuran, diethyl ether, benzene, toluene or mixture of them, at a temperature varying from about −78° C. to room temperature, preferably under an inert atmosphere of nitrogen or argon.

Successively the ylide so obtained is treated with the compound of formula (IV) and the reaction is continued at a temperature varying from room temperature to the reflux temperature of the mixture for a time varying from some hours to some days.

The reduction of a compound of formula (VII), according to a process variant C) may, for example, be performed by treating a compound of formula (VII) with tri-n-butyl tin hydride, sometimes in the presence of azobis(isobutyronitrile)(AIBN) as radical initiator, in a solvent such as, for example, toluene at a temperature ranging from room temperature to the reflux temperature of the solvent, for a time varying from 1 hour to 4 hours.

The hydrogenation of a compound of formula (I) according to the process variant D), may, for example, be carried out in a solvent such as, for example, methanol, ethanol, ethyl acetate, in the presence of about 10% to 30% of hydrogenation catalyst such as, for example, 5% Pd/C or 10% Pd/C, Ni-Raney, at a hydrogen pressure of 1 atmosphere at room temperature for a time varying from half an hour to 3 hours.

The dehydrogenation of a compound of formula (I) according to the process variant E), which is preferably performed on a compound of formula (I) wherein R is hydrogen, may be carried out by treatment with a suitable dehydrogenating agent such as, e.g., chloranil, benzeneseleninic anhydride or dichlorodicyanobenzoquinone (DDQ), operating in an anhydrous solvent, such as, for example, chlorobenzene, dioxane, xylene, toluene or benzene, and, optionally, in the presence of BSTFA [bis(trimethylsilyl)trifluoroacetamide]. The reaction temperature may range from the room temperature to the reflux temperature of the solvent and the reaction time may vary approximately from about 2 hours to about 24 hours.

Preferably the reaction is carried out under an inert atmosphere, e.g., a nitrogen atmosphere.

The compounds of formula (II) are known compounds or can be prepared from known compounds according to known procedure.

The compounds of formula (III) are commercially available or they can be synthesized by known methods. For example, by the reduction of the corresponding trifluoroamides (see JOC 24, 1256–59 (1959)) or from the corresponding ketones (Tetr. Lett. 31 (39), 5547–50 (1990)), or by reduction of the corresponding N-hydroxylamines (JOC 52, 3197 (1967)) or isocyanates (DE-A-3326875 and DE-A-3611195).

The compounds of formula (III), wherein $R_2$, $R_3$ and $R_5$ have all the meanings defined above, except hydrogen, and $R_1$ is hydrogen, Y is a single bond, and A and $R_4$ are fluorine atoms may be obtained by hydrolysis of a carbamate of formula (VIII)

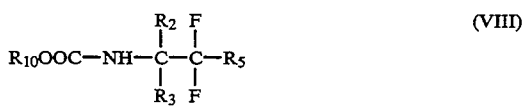

wherein $R_2$, $R_3$ and $R_5$ have all the meanings defined above, except hydrogen and $R_{10}$ is a $C_1$-$C_4$ alkyl group, preferably an ethyl group, or a benzyl group.

The hydrolysis is, for example, carried out by treatment of the carbamate in a solvent such as, for example, dioxane, tetrahyrofuran or ethanol with 48% hydrobromic acid, at the reflux temperature of the reaction mixture, for a time varying from 5 hours to 24 hours.

The carbamate of formula (VIII) is obtained by reacting a compound of formula (IX)

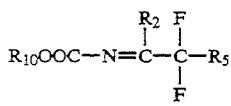 (IX)

wherein $R_{10}$, $R_2$ and $R_5$ are as defined above, with an organomagnesium compound of formula (X)

 (X)

wherein $R_3$ is as defined above, Mg is a magnesium atom and X is a halogen, preferably chlorine, bromine or iodine.

The reaction is carried out in an anhydrous solvent such as, for example, diethyleter or tetrahydrofuran, at a temperature ranging from −10° C. to the reflux temperature of the reaction mixture for a time varying from 30 minutes to 4 hours.

A compound of formula (IX) may be obtained reacting a compound of formula (XI)

$$R_{10}OOC-N=PPh_3 \quad (XI)$$

wherein $R_{10}$ is as defined above, with a compound of formula (XII):

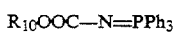 (XII)

wherein $R_2$ and $R_5$ are as defined above. The reaction between the azaphosphorane (XI) and the fluorinated ketone (XII) is carried out in the usual conditions reported in the literature for the aza-Wittig reaction.

The compounds of formulae (X), (XI) and (XII) are known compounds or they can be synthesized according to known methods.

The compounds of formula (IV) may be obtained, for instance, by reacting a compound of formula (II) with an α-amino ketone of formula (XIII)

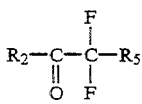 (XIII)

wherein $R_1$, $R_2$, $R_3$ and $R_5$ are as defined above. For example, the reaction is performed in an inert solvent such as, for example, methylene chloride, ethyl acetate, tetrahydrofuran, dimethylformamide, benzene or toluene at a temperature ranging from about 0° C. to about 100° C. optionally in the presence of an organic base such as, for example, pyridine, p-dimethylaminopyridine or triethylamine, for a time varying from half an hour to five days. The compounds of formula (XIII) are often used as N-salt-derivatives (for example, as hydrochlorides or trifluoroacetates). In that event, a stoichiometric amount of an organic base such as, for example, pyridine or a tri-$C_1$-$C_6$-alkylamine, preferably triethylamine, has to be added to the reaction mixture.

A compound of formula (VII) may be obtained by reaction of a compound of formula (XIV)

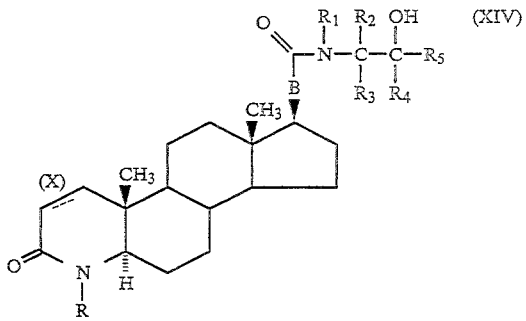 (XIV)

wherein the symbol $\doteq$, B, R, $R_1$, $R_2$, $R_3$, $R_5$ as defined above and $R_4$ is hydrogen, with a compound of formula (XV)

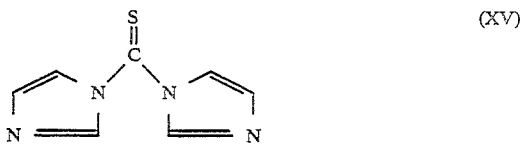 (XV)

The reaction is, for example, performed by refluxing a mixture of the alcohol of formula (XIV) and excess 1,1-thiocarbonyl diimidazole of formula (XV) in an anhydrous solvent such as, for example, 1,2-dichloroethane, methylene chloride or tetrahydrofuran for a time varying from about 1 hour to 8 hours, preferably under an inert atmosphere of, for example, nitrogen.

The compounds of formula (XIV) may be obtained, for instance, by reaction of a compound of formula (II) wherein the symbol $\doteq$ and R and B are as defined above with a compound of formula (XVI)

 (XVI)

wherein $R_1$, $R_2$, $R_3$ and $R_5$ are as defined above and $R_4$ is hydrogen.

The reaction may be carried out, for example, in a solvent such as, for example, methylene chloride or ethyl acetate, at a temperature ranging from about 0° C. to 70° C., optionally in the presence of an organic base such as, for example, a $C_1$-$C_6$ trialkylamine, preferably triethylamine, for a time varying from 2 hours to 24 hours.

The compounds of formula (XVI) are often used as salt-derivatives, preferably hydrochlorides, and the amino group is formed in situ in the presence of an organic base such as, for example, a $C_1$-$C_6$-trialkylamine, preferably triethylamine.

The compounds of formulae (XV) and (XVI) are commercially available compounds or may be obtained by known procedures.

The compounds of formulae (V), (VI), and (XIII) are known compounds or they can be synthesized by known methods.

The compounds of the present invention inhibit specifically the testosterone 5α-reductase enzyme and, therefore, are potent antiandrogens. For example, the inhibitory effect of the compounds of the invention on 5α-reductase was determined in vitro and in vivo according to the procedure reported herebelow.

In vitro assay of 5α-reductase inhibition

Inhibition of 5α-reductase was evaluated using the particulate fraction from homogenates of hyperplastic human prostates as the enzyme source. The particulate fraction was prepared centrifuging prostate homogenate at 140,000×g. The resulting pellet, washed several times, was resuspended in buffer and stored at −80° C. in aliquots containing ≈10 mg protein/ml.

The assay for 5α-reductase was done in a final volume of 0.5 ml, in 40 mM TRIS-HCl buffer pH 5.5, containing 1 mM dithiothreitol, 5 mM NADPH, 1 μM [$^{14}$C] testosterone, an aliquot of the enzyme preparation and various of the inhibitors. After 30 min incubation at 37° C. the reaction was terminated by addition of 2 ml cold diethyl ether and the organic phase was separated, evaporated under N$_2$ and resuspended in ethyl acetate. Testosterone metabolites in this extract were separated in TLC on silica gel F 254 plates (Merck), using chloroform, acetone and n-hexane (2:1:2) as developing solvent system.

Radioactivity on the plate was scanned and analyzed from quantitative plots printed by a TLC-analyzer (Berthold). The fractional 5α-reduction of testosterone was calculated by relating the $^{14}$C-radioactivity in the 5α-reduced metabolites (5α-dihydrotestosterone, 3α- and 3β-androstanediols) regions to the total radioactivity in the testosterone and 5α-reduced metabolites regions. The concentration of each compound required to reduce control 5α-reductase activity by 50% (IC$_{50}$) was determined by plotting % inhibition versus log of inhibitor concentration.

In vivo inhibition of 5α-reductase

The standard test for the antiandrogenic effect in rats was used. Prepuberal 22-day-old male rats were castrated via scrotal incision under light ether anaesthesia. On the seventh day after orchiectomy, androgen replacement was performed via subcutaneous implantation of 1 cm-long Silastic ® tube (Dow-Corning, Model No 602-265) filled with a mixture of 25% testosterone and 75% cholesterol. The rats were then treated orally with the tested compounds (7 animals/group), once daily for 7 consecutive days. 24 hours after the last dose the rats were sacrificed and the ventral prostate was removed and weighed. Control animals (testosterone controls) received the vehicle (0.5 ml/kg of 0.5% Methocel/0.4% Tween 80). One group of castrated rats was not implanted with testosterone (castrated controls).

The mean percentage of inhibition of the T-induced hypertrophic response of the prostate was calculated according to the following formula:

$$\% \text{ inhibition} = 100 \times (W_{TC} - W_1)/(W_{TC} - W_{CC})$$

where $W_{TC}$, $W_{CC}$ and $W_1$ are the mean prostate weight of testosterone control, castrated control and inhibitor treated group, respectively.

As an example, the results obtained with some representative compounds of the invention are shown in the following Table:

TABLE 1

In vitro and in vivo inhibition of 5α-reductase

| COMPOUND | IN VITRO INHIBITION IC$_{50}$ (nM) | % INHIBITION OF PROSTATE WEIGHT AT 3 mg/kg/day p.o. |
|---|---|---|
| 40 | 21 | 51 |
| 41 | 12 | 54 |

From the results reported in Table 1 it is evident that the new compounds are very potent 5α-reductase inhibitors, both in vitro and in vivo. In view of the above indicated activity the compounds of the invention are therapeutically useful in the situations in which a decrease in androgen action, by means of 5α-reductase inhibition, is desirable such as, for example, benign prostatic hyperplasia, prostatic and breast cancers and certain skin-hair conditions such as, e.g. acne, seborrhoea, female hirsutism and male pattern baldness. A mammal, e.g. a human or animal, may thus be treated by a method which comprises administering thereto a pharmaceutically effective amount of a compound of formula (I) as defined above.

The toxicity of the compounds of the invention is quite negligible so that they can be safely used in therapy. The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion; or topically, e.g. in the form of creams.

The dosage depends on the age, weight, conditions of the patient and administration route; for example the dosage adopted for oral administration to adult humans may range from about 1 to 200 mg pro dose, from 1 to 3 times daily.

As already said the invention includes pharmaceutical compositions comprising a compound of the invention in association with a pharmaceutically acceptable excipient (which can be carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; desegregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing granulating, tabletting, sugar-coating, or film-coating processes. The liquid dispersions for oral administration may be, e.g. syrups, emulsions and suspensions.

The syrups may contain as carrier, for example, saccharose or saccharose with glycerin and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycol, e.g. propylene glycol and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

Conventional carriers may be used for topical formulations.

The present invention further provides a compound of formula (I) for use in a method of treatment of the human or animal body by therapy, in particular for use as a testosterone 5α-reductase inhibitor.

The present invention further provides the use of a compound of formula (I) in the manufacture of a medicament for use as a testosterone 5α-reductase inhibitor.

The following Examples further illustrate the invention.

The reported NMR data are determined in deuterochloroform (CDCl$_3$), unless otherwise specified, and are reported as parts per million (δ) downfield from tetramethylsilane. According to the nomenclature used in the Examples the compounds are numbered as shown herebelow:

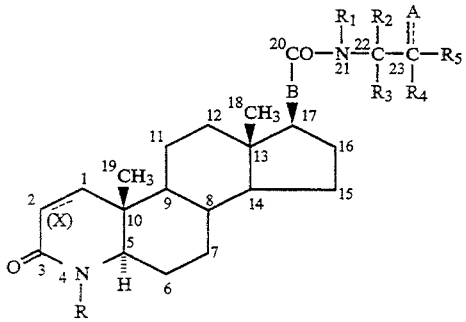

EXAMPLE 1

N-(2,2,2-trifluoroethyl) 3-oxo-4-aza-5α-androst-1-ene-17β-carboxamide [(I): X=double bond; Y=single bond; B=bond; R=H; R$_1$=H; R$_2$=H; R$_3$=H; R$_4$=F; R$_5$=F; A=F]

A mixture of 2-pyridyl 3-oxo-4-aza-5α-androst-1-ene-17β-carbothioate (102.5 mg) and 2,2,2-trifluoroethylamine (0.55 ml) in anhydrous tetrahydrofuran (2.5 ml) was refluxed for 4 hours.

The solvent was removed under vacuum and the yellow solid was purified by flash chromatography (eluent: ethyl acetate/methylene chloride 20:1) so obtaining 110 mg of the title compound as a white crystalline solid (m.p. 220°–221° C., methylene chloride).

NMR (CDCl$_3$, δ): 6.77 (d, 1H, H(1)), 5.8 (dd, 1H, H(2)), 5.56 (t, 1H, CONHCH$_2$CF$_3$), 5.52 (bs, 1H, NH), 4.18 and 3.70 (2m, 2H, CONHCH$_2$CF$_3$), 3.31 (dd, 1H, H(5α)), 0.96 (s, 3H, CH$_3$(19)), 0.78 (s, 3H, CH$_3$(18)).

MS (m/z):
398 M+•
383 M—•CH$_3$] +

Using the appropriate starting material and following an analogous procedure the compounds listed below were also prepared.

N-(4,4,4-trifluoro-3-methyl-but-2-yl) 4-methyl-3-oxo-4-aza-5α-androstane-17β-carboxamide;
N-(1,1,1-trifluoro-3-methyl-but-2-yl) 4-methyl-3-oxo-4-aza-5α-androstane-17β-carboxamide;
N-(4,4,4-trifluoro-3-methyl-but-2-yl) 3-oxo-4-aza-5α-androstane-17β-carboxamide;
N-(1,1,1-trifluoro-3-methyl-but-2-yl) 3-oxo-4-aza-5α-androstane-17β-carboxamide;
N-(5-methyl-2-difluoromethyl-hex-3-yl) 4-methyl-3-oxo-4-aza-5α-androstane-17β-carboxamide;
N-(3-difluoromethyl-hept-2-yl) 4-methyl-3-oxo-4-aza-5α-androstane-17β-carboxamide;
N-(5-methyl-2-difluoromethyl-hex-3-yl) 3-oxo-4-aza-5α-androstane-17β-carboxamide;
N-(3-difluoromethyl-hept-2-yl) 3-oxo-4-aza-5α-androstane-17β-carboxamide;
N-(4,4,4-trifluoro-3-methylene-but-2-yl) 4-methyl-3-oxo-4-aza-5α-androstane-17β-carboxamide;
N-(1,1,1-trifluoro-3-methylene-but-2-yl) 4-methyl-3-oxo-4-aza-5α-androstane-17β-carboxamide;
N-(4,4,4-trifluoro-3-methylene-but-2-yl) 3-oxo-4-aza-5α-androstane-17β-carboxamide;
N-(1,1,1-trifluoro-3-methylene-but-2-yl) 3-oxo-4-aza-5α-androstane-17β-carboxamide;
N-(5-methyl-2-difluoromethylene-hex-3-yl) 4-methyl-3-oxo-4-aza-5α-androstane-17β-carboxamide;
N-(3-difluoromethylene-hept-2-yl) 4-methyl-3-oxo-4-aza-5α-androstane-17β-carboxamide;
N-(5-methyl-2-difluoromethylene-hex-3-yl) 3-oxo-4-aza-5α-androstane-17β-carboxamide;
N-(3-difluoromethylene-hept-2-yl) 3-oxo-4-aza-5α-androstane-17β-carboxamide;
N,N-di-(2,2,2-trifluoroethyl) 3-oxo-4-aza-5α-androstan-1-ene-17β-carboxamide;
N-(1,1,1,3,3,3-hexafluoroprop-2-yl) 3-oxo-4-aza-5α-androst-1-ene-17β-carboxamide;
N,N-di-(1,1,1,3,3,3-hexafluoroprop-2-yl) 3-oxo-4-aza-5α-androst-1-ene-17β-carboxamide;
N-methyl-N-(2,2,2-trifluoroethyl) 3-oxo-4-aza-5α-androst-1-ene- 17β-carboxamide;
N-isobutyl-N-(2,2,2-trifluoroethyl) 3-oxo-4-aza-5α-androst-1-ene-17β-carboxamide;
N-(1-fluoro-2-methyl-prop-2-yl) 3-oxo-4-aza-5α-androst-1-ene-17β-carboxamide;
N-(1,3-difluoro-2-methyl-prop-2-yl) 3-oxo-4-aza-5α-androst-1-ene-17β-carboxamide;
N-(1,3-difluoro-2-fluoromethyl-prop-2-yl) 3-oxo-4-aza-5α-androst-1-ene-17β-carboxamide.

EXAMPLE 2

N-(2,2,2-trifluoroethyl)-4-methyl-3-oxo-4-aza-5α-androstane-17β-carboxamide [(I): X=single bond; Y=single bond; B=bond; R=CH$_3$; R$_1$=H; R$_2$=H; R$_3$=H; R$_4$=F; R$_5$=F; A=F]

To a suspension of 2,2,2-trifluoroethylamine hydrochloride (948.5 mg) in anhydrous tetrahydrofuran (10 ml), triethylamine (0.973 ml) was added. After stirring for 15 min at room temperature, solid 2-pyridyl 4-methyl-3-oxo-4-aza-5α-androstane-17β-carbothioate (426 mg) was added and the mixture was heated to reflux for 4 hours.

The volatiles were removed under vacuum and the crude was purified by flash chromatography on silica gel (eluent: ethylacetate/methylene chloride 20:1) to yield 330 mg of the title compound (m.p. 242-244° C.).

NMR (CDCl$_3$) δ: 6:5.65 (m, 1H, NH), 4.5–3.5 (m, 2H, CH$_2$CF$_3$), 3.1 (dd, 1H, H(5α)), 2.9 (s, 3H, N—CH$_3$), 0.87 (S, 3H, CH$_3$(19)) 0.67 (s, 3H, CH$_3$(18)).

Elemental analysis Calculated for C$_{22}$H$_{33}$F$_3$N$_2$O$_2$: C 63.75%, H 8.02%, N 6.76%. Found: C 63.44%, H 7.78%, N 6.67%.

Following an analogous procedure and using the appropriate starting materials the compounds listed below were prepared:
N-isopropyl-N-(2,2,2-trifluoroethyl) 3-oxo-4-aza-5α-androst-1-ene-17β-carboxamide;
N-isopropyl-N-(2,2,3,3,3-pentafluoropropyl) 3-oxo-4-aza-5α-androst-1-ene-17β-carboxamide.

EXAMPLE 3

(22RS)-N-(2,2,2-trifluorophenylethyl) 3-oxo-4-aza-5α-androst-1-ene-17β-carboxamide [(I):
X=double bond; Y=single bond; B=bond; R=H; R$_1$=H; R$_2$=Ph; R$_3$=H; R$_4$=F; R$_5$=F; A=F]

To a solution of (RS)-2,2,2-trifluorophenylethylamine hydrochloride (205 mg) in anhydrous dimethylformamide (4 ml), triethylamine (0.270 ml) was added.

After stirring at room temperature for 30 minutes, solid 2-pyridyl 3-oxo-4-aza-5α-androst-1-ene-17β-carbothioate (200 mg) was added and the mixture was heated to 100° C. for 8 hours.

The reaction mixture was diluted with water and extracted with ethylacetate; the organic extracts were washed with 1N hydrochloric acid, with water until neutral, dried over sodium sulphate and the solvent was evaporated under reduced pressure.

The residue was purified by flash chromatography on silica gel (eluent: ethylacetate/methylene chloride 20:1) to yield 125 mg of the title compound (m.p. 260°–265° C.).

NMR (CDCl$_3$) δ: 7.38 (s, 5H, Ph), 6.77 (d, 1H, H(1)), 5.95–5.70 (m, 3H, H(2)+NH(21)+CH(CF$_3$)Ph), 5.21 (s, 1H, NH(4)), 3.33 (dd, 1H, H(5α)), 0.99 and 0.94 (2s, 3H, CH$_3$(19)), 0.72 and 0.56 (2s, 3H, CH$_3$(18)) MS (m/z): 474 M+•, 459 M—•CH$_3$⎤ +, 454 M-HF⎤ +•.

Following an analogous procedure N-(1,3-difluoro-2-fluoromethylprop-2-yl) 3-oxo-4-aza-5α-androst-1-ene-17β-carboxamide was prepared.

EXAMPLE 4

(RS)-1-trifluoromethyl-1-phenyleth-1-ylamine hydrochloride [(III): Y=single bond; R$_1$=H; R$_2$=Ph; R$_3$=CH$_3$; R$_4$=F; R$_5$=F; A=F]

A mixture of trifluoroacetophenone [(XII): R$_2$=Ph, R$_5$=F] (1.536 ml), N-carbethoxytriphenylphosphinimine [(XI): R$_{10}$=Et] (3.494 g) in anhydrous toluene (25 ml) was heated to reflux for 24 hours.

The volatiles were removed under vacuum and the solid residue was suspended in diethylether/petroleum ether (50:50) and filtered; the filtrate was evaporated under vacuum to yield an oil (2.15 g) that was purified by chromatography on silica gel (eluent: petroleum ether/diethylether 3:1) so obtaining 1.40 g of N-carbethoxy-2,2,2-trifluoro-1-phenylethanimine [(IX): R$_{10}$=Et; R$_2$=Ph; R$_5$=F] as a colourless oil.

NMR (CDCl$_3$) δ: 7.3–7.7 (m, 5H, Ph), 4.25 (q, 2H, COOCH$_2$) 1.2 (t, 3H, COOCH$_2$CH$_3$).

IR (neat): 1725, 1680 cm$^{-1}$.

A solution of N-carbethoxy-2,2,2-trifluoro-1-phenylethanimine (210 mg) in anhydrous diethylether (5.0 ml) was added dropwise at room temperature to a freshly prepared 1M solution of methyl magnesium iodide in diethylether (8.0 ml); then the reaction mixture was refluxed for 0.5 hours and stirred at room temperature for 1 hour.

After cooling to 0° C. with an ice bath, the reaction was quenched with 1N hydrochloric acid (10 ml) and extracted with diethylether. The organic extracts were washed with water, 1N sodium thiosulphate, brine and dried over sodium sulphate. After removing the solvent under vacuum, the crude was purified by flash chromatography on silica gel (eluent petroleum ether/diethylether 4:1) to yield 730 mg of (RS)-ethyl N-(1-trifluoromethyl-1-phenylethyl) carbamate [(VIII) : R$_{10}$=Et; R$_2$=Ph; R$_3$=CH$_3$; R$_5$=F] as a white solid.

NMR (CDCl$_3$) δ: 7.3–7.6 (m, 5H, Ph), 5.55 (bs, 1H, NH), 4.05 (q, 2H, COOCH$_2$CH$_3$), 2.05 (m, 3H, PhCCH$_3$(CF$_3$)), 1.20 (t, 3H, COOCH$_2$CH$_3$).

MS (m/z): 261 M+•; 192 M—•CF$_3$⎤ +.

The carbamate (730 mg) dissolved in dioxane (6.0 ml) was treated with 48% hydrobromic acid (2 ml) and the mixture was heated to reflux for 16 hours.

After cooling and diluting with water the solution was washed with diethylether, basified to pH 12–13 with 1N sodium hydroxide and extracted with diethylether; the organic extracts were washed with brine and dried over sodium sulphate. The anhydrifier was filtered off, 2.2N hydrochloric acid (1 ml) was added and the solvent was removed under reduced pressure; the crude oil so obtained was crystallized from acetonitrile to afford 435 mg of the title compound.

MS (m/z): 189 M+•; 174 M—•CH$_3$⎤ +; 120 M—•CF$_3$⎤ +.

EXAMPLE 5

(22RS)-N-(1,1,1-trifluoro-2-phenylprop-2-yl) 3-oxo-4-aza-5α-androst-1-ene-17β-carboxamide [(I):
X=double bond; Y=single bond; B=bond; R=H; R$_1$=H; R$_2$=Ph; R$_3$=CH$_3$; R$_4$=F; R$_5$=F; A=F]

2-Pyridyl-3-oxo-4-aza-5α-androst-1-ene-17β-carbothioate (205 mg) was dissolved in methylene chloride (2.5 ml) containing methyl iodide (63 μl). After stirring at room temperature for 15 minutes, (RS)-1-trifluoromethyl-1-phenyleth-1-yl amine (160 mg), dissolved in 3 ml of DMF, was added and the mixture was heated at 100° C. for 8 hours. The reaction mixture was poured into water (75 ml) and extracted with methylene chloride.

The organic extracts were washed with 1N hydrochloric acid, with water and anhydrified over sodium sulphate and the solvent was evaporated at reduced pressure.

The solid residue was taken up with ethyl acetate: the insoluble solid was filtered off and the filtrate was chromatographed on silica gel (eluent: ethylacetate/methylene chloride 20:1) to yield 47 mg of the title compound, that solidified by treatment with n-pentane (m.p. 151°–155° C.).

NMR (CDCl$_3$) δ:7.48–7.35 (m, 5H, Ph), 6.79 (dd, 1H, H(1)) 5.88 (d, 1H, NH(21)), 5.81 (dd, 1H, H(2)), 5.48 (s, 1H, NH(4)) , 3.33 (dd, 1H, H(5α)) , 2.05 and 2.07 (2s, 3H, NHC$\underline{\text{H}}$3(CF3) Ph), 0.98 and 0.97 (28, 3H, CH3(19)), 0.72 and 0.68 (28, 3H, CH3(18)).

Ms(m/z): 488 M+•; 473 M−•C3 ⌉+; 173 •C(CF3)(CH3)Ph ⌉ +.

Following an analogous procedure and using the appropriate starting materials the following compounds were prepared:

N-(2,2,2-trifluoro-1,1-diphenylethyl) 3-oxo-4-aza-5α-androst-1-ene-17β-carboxamide;

N-(1,1,1-trifluoro-2-methylprop-2-yl) 3-oxo-4-aza-5α-androst-1-ene-17β-carboxamide;

N-(1,1,1,3,3,3-hexafluoro-2-methylpropyl) 3-oxo-4-aza-5α-androst-1-ene-17β-carboxamide.

EXAMPLE 6

(22RS) -N- (4,4,4-trifluoro-3-methylene-but-2-yl) 3-oxo-4-aza-5α-androst-1-ene-17β-carboxamide [(I): X=double bond; Y=double bond; B=bond; R=H; R1=H; R2=CH3; R3=H; R4 is absent; A=CHH2; R5=CF3]

Methyltriphenylphosphonium iodide (44 mg) was added portionwise to a stirred solution of potassium tertbutylate (9 mg) in dimethylsulphoxide (0.5 ml) maintained under nitrogen at room temperature.

After 10 minutes the yellow solution of the ylide so obtained was treated dropwise with a solution of (22RS)-N-(1,1,1-trifluoro-2-oxobut-3-yl) 3-oxo-4-aza-5α-androst-1-ene-17β-carboxamide (30 mg) in 1.5 ml of dimethylsulphoxide. The solution became clear in a few minutes.

After diluting with ethyl acetate, the reaction mixture was washed with water, dried over sodium sulphate and the solvent was evaporated at reduced pressure. The crude oil was purified by flash chromatography (eluent methylene chloride/acetone 50:50) to yield 21 mg of the title compound.

NMR (CDCl3) δ: 6.78 (d, 1H, H(1)), 5.80 (dd, 1H, H(2)), 5.75 (d, 1H, NH(21)), 5.55 (bs, 1H, NH(4)), 5.60 and 5.35 (2m, 2H, C=CH2) , 4.70 (m, 1H, NHC$\underline{\text{H}}$(CH3)), 3.33 (dd, 1H, H(5α)), 1.35 (d, 3H, NHCH(C$\underline{\text{H}}$3)), 0.97 (s, 3H, CH3(19)), 0.70 (s, 3H, CH3(18)).

Following an analogous procedure the compounds listed below were prepared:

N-(5,5,5-trifluoro-4-methylene-2-methylpent-3-yl) 3-oxo-4-aza-5α-androst-1-ene-17β-carboxamide;

N-(4,4,4-trifluoro-3-methylene-2-methylbut-2-yl)-3-oxo-4-aza-5α-androst-1-ene-17β-carboxamide;

N-(4,4,4-trifluoro-3-methylene-but-2-yl)-4-methyl-3-oxo-4-aza-5α-androstane-17β-carboxamide;

N-(1,1,1-trifluoro-3-methylene-but-2-yl)-4-methyl-3-oxo-4-aza-5α-androstane-17β-carboxamide;

N-(4,4,4-trifluoro-3-methylene-but-2-yl)-3-oxo-4-aza-5α-androstane-17β-carboxamide;

N-(1,1,1-trifluoro-3-methylene-but-2-yl)-3-oxo-4-aza-5α-androstane-17β-carboxamide.

EXAMPLE 7

(22RS-23RS)-N-(4,4,4-trifluoro-3-methylbut-2-yl) 3 -oxo-4 -aza-5α-androstane-17β-carboxamide [(I): X =single bond; Y =single bond; B=bond; R=H; R1=H; R2=CH3; R3=H; R4=H; A=CH3; R5=CF3]

A solution of (22R,S)-N-(2-trifluoromethyl-but-1-en-3-yl) 3-oxo-4-aza-5α-androst-1-ene-17β-carboxamide (21 mg) in ethyl acetate was hydrogenated under pressure (30 psi) at room temperature for 3 hours, in the presence of 10% Pd/C (4 mg).

The catalyst was filtered off and the solvent was evaporated under vacuum.

The residue was chromatographed on silica gel (eluent methylene chloride/acetone 50:50) to yield 16 mg of the title compound.

NMR (CDCl3) 6:5.67 (s, 1H, NH(4)), 5.30 (d, 1H, NH(21)), 4.35 (m, 1H, NHC$\underline{\text{H}}$(CH3)), 3.03 (dd, 1H, H(5α)), 2.35 (m, 1H, —C$\underline{\text{H}}$(CH3)CF3), 1.23 (2d, 6H, NHCH(C$\underline{\text{H}}$3)CH(C$\underline{\text{H}}$3) CF3), 0.87 (s, 3H, CH3(19)), 0.70 (s, 3H, C$\underline{\text{H}}$3(18)).

Following an analogous procedure the following compounds were prepared:

N-(5,5,5-trifluoro-2,4-dimethylpent-3-yl) 3-oxo-4-aza-5α-androstane-17β-carboxamide;

N-(4,4,4-trifluoro-2,3-dimethylbut-2-yl) 3-oxo-4-aza-5α-androstane-17β-carboxamide;

N-(4,4,4-trifluoro-3-methyl-but-2-yl) 4-methyl-3-oxo-4-aza-5α-androstane-17β-carboxamide;

N-(1,1,1-trifluoro-3-methyl-but-2-yl) 4-methyl-3-oxo-4-aza-5α-androstane-17β-carboxamide;

N-(1,1,1-trifluoro-3-methyl-but-2-yl) 3-oxo-4-aza-5α-androstane-17β-carboxamide;

N-(5-methyl-2-difluoromethyl-hex-3-yl)4-methyl-3-oxo-4-aza-5α-androstane-17β-carboxamide;

N-(3-difluoromethyl-hept-2-yl) 4-methyl-3-oxo-4-aza-5α-androstane-17β-carboxamide;

N-(5-methyl-2-difluoromethyl-hex-3-yl) 3-oxo-4-aza-5α-androstane-17β-carboxamide;

N-(3-difluoromethyl-hept-2-yl) 3-oxo-4-aza-5α-androstane-17β-carboxamide.

EXAMPLE 8

N-(4,4,4-trifluoro-3-methylbut-2-yl) 3-oxo-4-aza-5α-androst-1-ene-17β-carboxamide [(I) : X=double bond; Y=single bond; B=bond; R=H; R1=H; R2=CH3; R3=H; R4=H; A=CHH3; R5=CF3]

To N-(4,4,4-trifluoro-3-methylbut-2-yl) 3-oxo-4-aza-5α-androstane-17β-carboxamide [(I): X=single bond; B=single bond; Y=single bond; R=H; R1=H; R2=CH]; R3=H; R4=H; A=CHH]; R5=CF3] (55 mg) suspended in chlorobenzene (5.0 ml), benzeneseleninic acid anhydride (64 mg) was added and the mixture was refluxed for 4 hours.

The solvent was removed under vacuum and the residue was dissolved in methylene chloride; the organic solution was washed with sodium bicarbonate, with saturated sodium chloride, anhydrified over sodium sulphate and the solvent was evaporated under reduced pressure.

Purification of the brown crude by chromatography on silica gel (eluent methylene chloride/ethyl acetate/methanol 50:45:5) afforded 28 mg of the title compound.

NMR (CDCl3) δ: 6.78 (d, 1H, H(1)), 5.80 (dd, 1H, H(2)), 5.67 (s, 1H, NH(21)), 5.30 (d, 1H, NH(21)), 4.35 (m, 1H, NHC$\underline{\text{H}}$(CH3)—), 3.33 (dd, 1H, H(5α)), 2.35 (m, 1H, C$\underline{\text{H}}$(CH3) CF3), 1.23 (2d, 6H, NHCH(C$\underline{\text{H}}$3)CH(CH3)CF3), 0.97(s, 3H, CH3(19)), 0.68 (s, 3H, CH3(18)).

Following an analogous procedure the compounds listed below were prepared:

N-(5,5,5-trifluoro-2,4-dimethylpent-3-yl) 3-oxo-4-aza-5α-androst-1-ene-17β-carboxamide;

N-(4,4,4-trifluoro-2,3=dimethylbut-2-yl) 3-oxo-4-aza-5α-androst-1-ene-17β-carboxamide.

EXAMPLE 9

(22RS)-N-(4,4,4-trifluorobut-2-yl) 3-oxo-4-aza-5α-androst- 1-ene-17β-carboxamide [(I): X=double bond; Y=single bond; B=bond; R=H; $R_1$=H; $R_2$=$CH_3$; $R_3$=H; $R_4$=H; A=H; $R_5$=$CF_3$]

(22RS-23RS) -N- (4,4,4-trifluoro-3-hydroxybut-2-yl) 3-oxo-4-aza-5α-androst-1-ene-17β-carboxamide [(XIV): X=double bond; B=single bond; R=H; $R_1$=H; $R_2$=$CH_3$; $R_4$=H; $R_4$=H; $R_5$=$CF_3$] (50 mg) was dissolved in 1,2-dichloromethane (1.3 ml) at room temperature under an inert atmosphere of nitrogen; solid 90% 1,1'-thiocarbonyldiimidazole (45 mg) was added and the mixture was heated at 75° C. (oil bath temperature) for 3 hours.

Purification of the reaction mixture by flash chromatography on silica gel (eluent: methylene chloride/ethylacetate/methanol 50:45:5) yielded 61 mg of (22RS-23RS)-N-[4,4,4-trifluoro-3-{[(imidazol-1yl)thiocarbonyl]oxy}but-2-yl] 3-oxo-4-aza-5α-androst-1-ene-17β-carboxamide [(VII): X=double bond; B=bond; R=H; $R_1$=H; $R_2$=$CH_3$; $R_3$=H; $R_4$=H; $R_5$=$CF_3$].

Tributyltin hydride (0.049 ml) in toluene (2.5 ml) was heated at reflux and a solution of N-[4,4,4-trifluoro-3-{[(imidazol-1-yl)thiocarbonyl]oxy}but-2-yl] 3-oxo-4-aza-5α-androst-1-ene-17β-carboxamide (51 mg) in toluene (1.3 ml) was added dropwise over 15 minutes and the mixture was refluxed for 85 minutes.

The solvent was removed under reduced pressure and the residue was purified by flash chromatography on silica gel (eluent methylene chloride/ethyl acetate/methanol 50:45:5) to give the title product (27 mg).

MS (m/z): 426 M+•; 411 M−•$CH_3$⌉ +.

NMR ($CDCl_3$) δ:6.78 (d, 1H, H(1)), 5.80 (dd, 1H, H(2)), 5.67 (s, 1H, NH(4)), 5.30 (d, 1H, NH(21)), 4.35 (m, 1H, —NHC̲H($CH_3$)—), 3.33 (dd, 1H, H(5α)), 2.42 and 2.28 (2m, 2H, —C̲H$_2$$CF_3$), 1.25 (d, 3H, —NHCH(C̲H$_3$)—), 0.97 (s, 3H, Me(19)), 0.68 (s, 3H, Me(18)).

Following an analogous procedure and using the appropriate starting materials the compounds listed below were prepared:

N-(5,5,5-trifluoro-2-methylpent-3-yl) 3-oxo-4-aza-5α-androst-1-ene-17β-carboxamide;

N-(4,4,4-trifluoro-2-methylbut-2-yl) 3-oxo-4-aza-5α-androst-1-ene-17β-carboxamide.

EXAMPLE 10

Scored tablets for oral use, each containing 250 mg of the active substance, were manufactured as follows:

| Composition (for 10,000 tablets) | |
|---|---|
| N-(2,2,2-trifluorophenylethyl) 3-oxo-4-aza-5α-androst-1-ene-17β-carboxamide | 2500 g |
| corn starch | 275 g |
| talc powder | 187 g |
| calcium stearate | 38 g |

The active substance was granulated with a 4% w/v aqueous solution of methyl cellulose. To the dried granules a mixture of the remainder of the ingredients is added and the final mixture compressed into tables of proper weight.

EXAMPLE 11

Two-piece hard gelatin capsules for oral use, each containing 250 mg of active substance were manufactured as follows.

| Composition for 10,000 capsules | |
|---|---|
| N-(2,2,2-trifluorophenylethyl) 3-oxo-4-aza-5α-androst-1-ene-17β-carboxamide | 2500 g |
| lactose | 1000 g |
| corn starch | 300 g |
| talc powder | 65 g |
| calcium stearate | 35 g |

The active substance was mixed with the starch-lactose mixture followed by the talc and calcium stearate.

EXAMPLE 12

Scored tablets for oral use, each containing 250 mg of the active substance, were manufactured as follows.

| Composition (for 10,000 tablets) | |
|---|---|
| N-(2,2,2-trifluorophenylethyl) 3-oxo-4-aza-5α-androst-1-ene-17β-carboxamide | 2500 g |
| corn starch | 280 g |
| talc powder | 180 g |
| calcium stearate | 40 g |

The active substance was granulated with a 4% w/v aqueous solution of methyl cellulose. To the dried granules a mixture of the remainder of the ingredients is added and the final mixture compressed into tables of proper weight.

We claim:
1. A compound of formula (I)

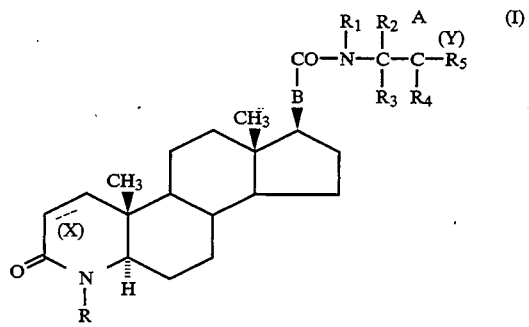

wherein:
the symbols ⚌ independently represent a single or a double bond;

B is a bond or a straight or branched $C_1$–$C_6$ alkylene chain;

R is a hydrogen atom or a $C_1$–$C_4$ alkyl group;

$R_1$ is a hydrogen atom, a $C_1$–$C_6$ alkyl group unsubstituted or substituted by one or more fluorine atoms, or a benzyl group;

$R_2$ is
a) a hydrogen atom, a fluorine atom, a $C_1$–$C_6$ alkyl group unsubstituted or substituted by one or more fluorine atoms, a $C_5$–$C_7$ cycloalkyl group or a $C_1$–$C_9$ cycloalkylalkyl group; or
b) a phenyl or benzyl group, either unsubstituted or ring substituted by one or more substituents chosen from $C_1$-$C_4$ alkyl, $C_1$-$C_4$ alkoxy, hydroxy and trifluoromethyl;

$R_3$ is
a) a hydrogen atom, a fluorine atom or a $C_1$-$C_4$ alkyl group unsubstituted or substituted by one or more fluorine atoms; or
b) a phenyl or benzyl group, either unsubstituted or ring substituted by one or more substituents chosen from $C_1$-$C_4$ alkyl, $C_1$-$C_4$ alkoxy, hydroxy and trifluoromethyl;

$R_4$ is a hydrogen atom or a fluorine atom, or is absent when Y is a double bond;

$R_5$ is a hydrogen atom, a fluorine atom or a $C_1$-$C_6$ alkyl group unsubstituted or substituted by one or more fluorine atoms; and when Y is a single bond, A is hydrogen, fluorine or a

group wherein each of $R_6$, $R_7$ and $R_8$ independently is hydrogen, fluorine or a $C_1$-$C_6$ alkyl group unsubstituted or substituted by one or more fluorine atoms; or when Y is a double bond, A is a

group wherein each of $R_6$ and $R_7$ is independently hydrogen, fluorine or a $C_1$-$C_6$ alkyl group unsubstituted or substituted by one or more fluorine atoms;

with the proviso that at least one of the groups $R_1$, $R_2$, $R_3$, $R_4$, $R_5$ or A has at least one fluorine atom.

2. A compound of formula (I) according to claim 1 wherein:

the symbol ≂ represents a single or a double bond;
B is a bond;
R is hydrogen or methyl or;
$R_1$ is hydrogen;
$R_2$ is hydrogen, methyl, isopropyl, isobutyl, sec-butyl, tert-butyl, trifluoromethyl, 3,3,3-trifluoropropyl, 4,4,4-trifluorobutyl, 2-trifluoromethylprop-1-yl, 1-trifluoromethyleth-1-yl, fluoromethyl, benzyl or phenyl;
$R_3$ is hydrogen or methyl;
$R_4$ is hydrogen;
$R_5$ is methyl, trifluoromethyl or n-butyl;
Y is a single bond; and
A is a group

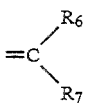

wherein $R_5$ is hydrogen or fluorine and $R_7$ and $R_8$ are both hydrogen or fluorine atoms;
with the proviso that at least one of the groups $R_2$, $R_5$ or A has at least one fluorine atom.

3. A compound of formula (I), according to claim 1, wherein:

the symbol ≂ represents a single or a double bond;
B is a bond;
R is hydrogen or methyl or;
$R_1$ is hydrogen;
$R_2$ is hydrogen, methyl, isopropyl, isobutyl, sec-butyl, tert-butyl, trifluoromethyl, 3,3,3-trifluoropropyl, 4,4,4-trifluorobutyl, 2-trifluoromethylprop-1-yl, 1-trifluoromethyleth-1-yl, fluoromethyl, benzyl, phenyl;
$R_3$ is hydrogen;
$R_4$ is absent;
$R_5$ is methyl, trifluoromethyl or n-butyl;
Y is a double bond; and
A is a group

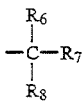

wherein $R_7$ and $R_8$ are both hydrogen atoms or fluorine atoms;
with the proviso that at least one of the groups $R_2$, $R_5$ or A has at least one fluorine atom.

4. A compound of formula (I) according to claim 1 wherein:

the symbol ≂ represents a single or a double bond;
R is hydrogen or methyl;
$R_1$ is hydrogen, 2,2,2-trifluoroethyl, 2,2,3,3,3-pentafluoroprop-1-yl, methyl, ethyl, isopropyl, isobutyl or tert-butyl;
$R_2$ is hydrogen, methyl, isopropyl, fluoromethyl, trifluoromethyl, benzyl or phenyl;
$R_3$ is hydrogen, methyl, fluoromethyl, trifluoromethyl, benzyl or phenyl;
$R_4$ is hydrogen or fluorine;
$R_5$ is hydrogen, fluorine or trifluoromethyl;
B is a bond;
Y is a single bond; and
A is hydrogen or fluorine;
with the proviso that at least one of the groups $R_1$, $R_2$, $R_3$, $R_4$, $R_5$ or A has a fluorine atom.

5. A compound selected from:
N-(4,4,4-trifluoro-3-methyl-but-2-yl) 4-methyl-3-oxo-4-aza-5α-androstane-17β-carboxamide;
N-(1,1,1-trifluoro-3-methyl-but-2-yl) 4-methyl-3-oxo-4-aza-5α-androstane-17β-carboxamide;
N-(4,4,4-trifluoro-3-methyl-but-2-yl) 3-oxo-4-aza-5α-androstane-17β-carboxamide;
N-(1,1,1-trifluoro-3-methyl-but-2-yl) 3-oxo-4-aza-5α-androstane-17β-carboxamide;
N-(5-methyl-2-difluoromethyl-hex-3-yl) 4-methyl-3-oxo-4-aza-5α-androstane-17β-carboxamide;
N-(3-difluoromethyl-hept-2-yl) 4-methyl-3-oxo-4-aza-5α-androstane-17β-carboxamide;
N-(5-methyl-2-difluoromethyl-hex-3-yl) 3-oxo-4-aza-5α-androstane-17β-carboxamide;
N-(3-difluoromethyl-hept-2-yl) 3-oxo-4-aza-5α-androstane-17β-carboxamide;
N-(4,4,4-trifluoro-3-methylene-but-2-yl) 4-methyl-3-oxo-4-aza-5α-androstane-17β-carboxamide;
N-(1,1,1-trifluoro-3-methylene-but-2-yl) 4-methyl-3-oxo-4-aza-5α-androstane-17β-carboxamide;
N-(4,4,4-trifluoro-3-methylene-but-2-yl) 3-oxo-4-aza-5α-androstane-17β-carboxamide;

N-(1,1,1-trifluoro-3-methylene-but-2-yl) 3-oxo-4-aza-5α-androstane-17β-carboxamide;

N-(5-methyl-2-difluoromethylene-hex-3-yl) 4-methyl-3-oxo-4-aza-5α-androstane-17β-carboxamide;

N-(3-difluoromethylene-hept-2-yl) 4-methyl-3-oxo-4-aza-5α-androstane-17β-carboxamide;

N-(5-methyl-2-difluoromethylene-hex-3-yl) 3-oxo-4-aza-5α-androstane-17β-carboxamide;

N-(3-difluoromethylene-hept-2-yl) 3-oxo-4-aza-5α-androstane-17β-carboxamide;

N-(2,2,2-trifluoroethyl) 3-oxo-4-aza-5α-androst-1-ene-17β-carboxamide;

N,N-di-(2,2,2-trifluoroethyl) 3-oxo-4-aza-5α-androst-1-ene-17β-carboxamide;

N-(1,1,1,3,3,3-hexafluoroprop-2-yl) 3-oxo-4-aza-5α-androst-1-ene-17β-carboxamide;

N,N-di-(1,1,1,3,3,3-hexafluoroprop-2-yl) 3-oxo-4-aza-5α-androst-1-ene-17β-carboxamide;

N-methyl-N-(2,2,2-trifluoroethyl) 3-oxo-4-aza-5α-androst-1-ene-17β-carboxamide;

N-isobutyl-N-(2,2,2-trifluoroethyl) 3-oxo-4-aza-5α-androst-1-ene-17β-carboxamide;

N-(1-fluoro-2-methyl-prop-2-yl) 3-oxo-4-aza-5α-androst-1-ene-17β-carboxamide;

N-(1,3-difluoro-2-methyl-prop-2-yl) 3-oxo-4-aza-5α-androst-1-ene-17β-carboxamide;

N-(1,3-difluoro-2-fluoromethyl-prop-2-yl) 3-oxo-4-aza-5α-androst-1-ene-17β-carboxamide;

N-(5,5,5-trifluoro-2,4-dimethylpent-3-yl) 3-oxo-4-aza-5α-androstane-17β-carboxamide;

N-(4,4,4-trifluoro-2,3-dimethylbut-2-yl) 3-oxo-4-aza-5α-androstane-17β-carboxamide;

N-(4,4,4-trifluoro-3-methylbut-2-yl) 3-oxo-4-aza-5α-androst-1-ene-17β-carboxamide;

N-(5,5,5-trifluoro-2,4-dimethylpent-3-yl) 3-oxo-4-aza-5α-androst-1-ene-17β-carboxamide;

N-(4,4,4-trifluoro-2,3-dimethylbut-2-yl) 3-oxo-4-aza-5α-androst-1-ene-17β-carboxamide;

N-(4,4,4-trifluorobut-2-yl) 3-oxo-4-aza-5¢-androst-1-end-17β-carboxamide;

N-(5,5,5-trifluoro-2-methylpent-3-yl) 3-oxo-4-aza-5α-androst-1-ene-17β-carboxamide;

N-(4,4,4-trifluoro-2-methylbut-2-yl) 3-oxo-4-aza-5α-androst-1-ene-17β-carboxamide;

N-(4,4,4-trifluoro-3-methylene-but-2-yl) 3-oxo-4-aza-5α-androst-1-ene-17β-carboxamide;

N-(5,5,5-trifluoro-4-methylene-2-methylpent-3-yl) 3-oxo-4-aza-5α-androst-1-ene-17β-carboxamide;

N-(4,4,4-trifluoro-3-methylene-2-methylbut-2-yl) 3-oxo-4-aza-5α-androst-1-ene-17β-carboxamide;

N-(2,2,2-trifluoroethyl) 4-methyl-3-oxo-4-aza-5α-androstane-17β-carboxamide;

N-isopropyl-N-(2,2,2-trifluoroethyl) 3-oxo-4-aza-5α-androst-1-ene-17β-carboxamide;

N-isopropyl-N-(2,2,3,3,3-pentafluoropropyl) 3-oxo-4-aza-5α-androst-1-ene-17β-carboxamide;

N-(2,2,2-trifluorophenylethyl) 3-oxo-4-aza-5α-androst-1-ene-17β-carboxamide;

N-(1,1,1-trifluoro-2-phenylprop-2-yl) 3-oxo-4-aza-5α-androst-1-ene-17β-carboxamide;

N-(2,2,2-trifluoro-1,1-diphenylethyl) 3-oxo-4-aza-5α-androst-1-ene-17β-carboxamide;

N-(1,1,1-trifluoro-2-methylprop-2-yl) 3-oxo-4-aza-5α-androst-1-ene-17β-carboxamide; and N-(1,1,1,3,3,3-hexafluoro-2-methylpropyl) 3-oxo-4-aza-5α-androst-1-ene-17β-carboxamide.

6. A pharmaceutical composition for inhibition of testosterone 5α-reductase comprising a pharmaceutical acceptable carrier and/or diluent and, as an active principle, an effective amount of a compound of formula (I) according to claim 1 to achieve said inhibition.

* * * * *

UNITED STATES PATENT AND TRADEMARK OFFICE
CERTIFICATE OF CORRECTION

PATENT NO. : 5,407,939

DATED : April 18, 1995

INVENTOR(S) : Panzeri Et Al

It is certified that error appears in the above-identified patent and that said Letters Patent is hereby corrected as shown below:

After the Abstract on
page 1, line 1 replace Formula I with --

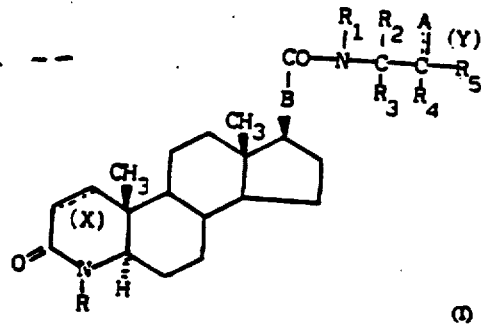

(I)

Column 2, line 1 replace Formula I with --

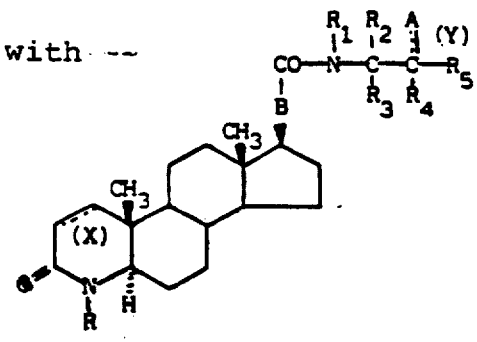

(I)

UNITED STATES PATENT AND TRADEMARK OFFICE
CERTIFICATE OF CORRECTION

PATENT NO. : 5,407,939
DATED : April 18, 1995
INVENTOR(S) : Panzeri Et Al

It is certified that error appears in the above-identified patent and that said Letters Patent is hereby corrected as shown below:

Column 4, line 14 "1,1,1,3,3,3-hexafldoroprop-2-yl," should read --1,1,1,3,3,3-hexafluoroprop-2-yl,--.

Column 15, line 10 "protein/mi" should read --protein/ml--.

Column 21, line 3 "•C$_3$" should read -- •CH$_3$--.

Column 21, line 19 "CHH$_2$" should read --CH$_2$--.

Column 22, line 38 "CHH$_3$" should read --CH$_3$--.

Column 22, line 43 "CHH];" should read --CH$_3$;--.

UNITED STATES PATENT AND TRADEMARK OFFICE
CERTIFICATE OF CORRECTION

PATENT NO. : 5,407,939
DATED : April 18, 1995
INVENTOR(S) : Panzeri Et Al

It is certified that error appears in the above-identified patent and that said Letters Patent is hereby corrected as shown below:

Column 24, Claim 1, replace Formula I with --

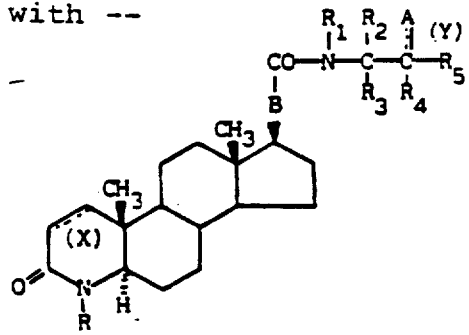

Signed and Sealed this

Twenty-eighth Day of November 1995

Attest:

BRUCE LEHMAN

Attesting Officer        Commissioner of Patents and Trademarks